(12) United States Patent
Zhang et al.

(10) Patent No.: US 8,597,902 B2
(45) Date of Patent: Dec. 3, 2013

(54) PEPTIDE PROTECTION AGAINST ULTRAVIOLET LIGHT TOXICITY

(75) Inventors: Lijuan Zhang, Kenmore, WA (US); Timothy J. Falla, Woodinville, WA (US)

(73) Assignee: Helix Biomedix, Inc., Bothell, WA (US)

( * ) Notice: Subject to any disclaimer, the term of this patent is extended or adjusted under 35 U.S.C. 154(b) by 0 days.

(21) Appl. No.: 13/508,564

(22) PCT Filed: Nov. 18, 2010

(86) PCT No.: PCT/US2010/057177
§ 371 (c)(1),
(2), (4) Date: May 8, 2012

(87) PCT Pub. No.: WO2011/063090
PCT Pub. Date: May 26, 2011

(65) Prior Publication Data
US 2012/0225023 A1    Sep. 6, 2012

Related U.S. Application Data

(60) Provisional application No. 61/262,790, filed on Nov. 19, 2009.

(51) Int. Cl.
G01N 33/53  (2006.01)
A01N 61/00  (2006.01)
A61K 31/00  (2006.01)
A61K 38/00  (2006.01)
C07K 14/47  (2006.01)

(52) U.S. Cl.
USPC .............................. 435/7.71; 514/1; 514/7.5

(58) Field of Classification Search
None
See application file for complete search history.

(56) References Cited

U.S. PATENT DOCUMENTS 5,962,417 A * 10/1999 Gilchrest et al. ............... 514/7.5
2009/0047335 A1  2/2009 Rastelli et al.

FOREIGN PATENT DOCUMENTS

WO         9735998 A1    10/1997

OTHER PUBLICATIONS

Eipper, B. Stoffers, D. and Mains, R. The Biosynthesis of Neuropeptides: Peptide a-Amidation Annu Rev NeuroSci 1992 15:57-85.*
Park, HY "Protein kinase C-B activates tyrosinase by phosphorylating serine residues in its cytoplasmic doman" 1999 Journal of Biological Chemistry 274: 16470-16478.*
International Search Reported dated Jun. 15, 2011, in international Application No. PCT/US10/57177.
Black et al., Protein Kinase C-Mediated Regulation of the Cell Cycle, Frontiers in Bioscience, Apr. 2, 2000, pp. 406-423, vol. 5, Abstract, Figure 2 (p. 408, col. 1, Para 3), (p. 408, col. 2, Para 4), (p. 412, col. 2, Para 2), (p. 417, col. 2, Para 1).
Park et al., Topical Application of a Protein Kinase C Inhibitor Reduces Skin and Hair Pigmentation, Journal of Investigative Dermatology, 2004, pp. 159-166, vol. 122, Abstract (p. 163).
Glass, David B., et al. "Primary Structural Determinants Essential for Potent Inhibition of cAMP-dependent Protein Kinase by Inhibitory Peptides Corresponding to the Active Portion of the Heat-stable Inhibitor Protein", The Journal of Biological Chemistry, vol. 264, No. 15, Issue of May 25, pp. 8802-8810, 1989.
Hoeben, Ann, et al. "Vascular endothelial growth factor and angiogenesis" Pharmacological Reviews, Williams and Wilkins Co., Vo. 56, No. 4, Dec. 1, 2004, pp. 549-580.
Santiago-Walker, Ademi E., et al. "Protein Kinase C. Stimulates Apoptosis by Initiating G1 Phase Cell Cycle Progression and S Phase Arrest*", The Jornal of Biological Chemistry, vol. 280 No. 37 pp. 32107-32114, Sep. 16, 2005.
European Search Report for Application No. 10832158.9 dated May 7, 2013.

* cited by examiner

*Primary Examiner* — John S Brusca
*Assistant Examiner* — Gerard Lacourciere
(74) *Attorney, Agent, or Firm* — Novak Druce Connolly Bove + Quigg LLP

(57) ABSTRACT

Short peptides having biological and therapeutic activity are disclosed. Specifically, the activity of the disclosed peptides is directed to reducing or protecting against mutagen-induced cellular/tissue toxicity (i.e., chemopreventive). For example, the disclosed peptides protect against skin toxicity and/or mutagenesis that occurs from ultraviolet (UV) light exposure. The disclosed peptides also block the activation of certain cell cycle regulatory proteins such as Chk2. An example of such a peptide is Ser-Leu-Tyr-Gln-Ser (SEQ ID NO: 10). The disclosed peptides are also useful for methods of reducing or protecting against cellular toxicity and mutation accumulation that would otherwise occur following mutagen exposure. One such method is drawn to applying a peptide to the skin to prevent or reduce mutagenic damage resulting from UV light (e.g., sunlight) exposure.

10 Claims, 5 Drawing Sheets

```
    SEQ ID NO:11
  1 mllavlycll wsfqtsaghf pracvssknl mekeccppws gdrspcgqls grgscqnill
 61 snaplgpqfp ftgvddresw psvfynrtcq csgnfmgfnc gnckfgfwgp ncterrllvr
121 rnifdlsape kdkffayltl akhtissdyv ipigtygqmk ngstpmfndi niydlfvwmh
181 yyvsmdallg gyeiwrdidf aheapaflpw hrlfllrweq eiqkltgden ftipywdwrd
241 aekcdictde ymggqhptnp nllspasffs swqivcsrle eynshqslcn gtpegplrrn
301 pgnhdksrtp rlpssadvef clsltqyesg smdkaanfsf rntlegfasp ltgiadasqs
361 smhnalhiym ngtmsqvqgs andpifllhh afvdsifeqw lrrhrplqev ypeanapigh
421 nresymvpfi plyrngdffi sskdlgydys ylqdsdpdsf qdyiksyleq asriwswllg
481 aamvgavlta llaglvsllc rhkrkqlpee kqpllmekedyhslyqshl
                                         hslyqsh   (SEQ ID NO:8)
                                          hslyqs   (SEQ ID NO:9)
                                            slyqs  (SEQ ID NO:10)
                                         fkslyqs   (SEQ ID NO:7)
                                         fhsiyqsh  (SEQ ID NO:6)
                                         yhslyesk  (SEQ ID NO:5)
                                        yhslyqshl  (SEQ ID NO:2)
                                        dfhslfqsh  (SEQ ID NO:4)
                                        yhsiyqshi  (SEQ ID NO:3)
                                       dyhtlyqthl  (SEQ ID NO:1)
```

FIG. 1

Human Chk2 (SEQ ID NO:17)
```
  1  msresdveaq qshgssacsq phgsvtqsqg sssqsqgiss sststmpnss qsshsssgtl
 61  ssletvstqe lysipedqep edqepeeptp apwarlwalq dgfanlecvn dnywfgrdks
121  ceycfdepll krtdkyrtys kkhfrifrev gpknsyiayi edhsgngtfv ntelvgkgkr
181  rplnnnseia lslsrnkvfv ffdltvddqs vypkalrdey imsktlgsga cgevklafer
241  ktckkvaiki iskrkfaigs areadpalnv eteieilkkl nhpciikikn ffdaedyyiv
301  lelmeggelf dkvvgnkrlk eatcklyfyq mllavqylhe ngiihrdlkp envllssqee
361  dclikitdfg hskilgetsl mrtlcgtpty lapevlvsvg tagynravdc wslgvilfic
421  lsgyppfseh rtqvslkdqi tsgkynfipe vwaevsekal dlvkkllvvd pkarftteea
481  lrhpwlqded mkrkfqdlls eenestalpq vlaqpstsrk rpregeaega ettkrpavca
541  avl
```

FIG. 3

Human Chk1 (SEQ ID NO:18)

```
  1  mavpfvedwd lvqtlgegay gevqlavnrv teeavavkiv dmkravdcpe nikkeicink
 61  mlnhenvvkf yghrregniq ylfleycsgg elfdriepdi gmpepdaqrf fhqlmagvvy
121  lhgigithrd ikpenlllde rdnlkisdfg latvfrynnr erllnkmcgt lpyvapellk
181  rrefhaepvd vwscgivlta mlagelpwdq psdscqeysd wkekktylnp wkkidsapla
241  llhkilvenp saritipdik kdrwynkplk kgakrprvts ggvsespsgf skhiqsnldf
301  spvnsassee nvkysssqpe prtglslwdt spsyidklvq gisfsqptcp dhmllnsqll
361  gtpgssqnpw qrlvkrmtrf ftkldadksy qclketcekl gyqwkkscmn qvtisttdrr
421  nnklifkvnl lemddkilvd frlskgdgle fkrhflkikg klidivssqk vwlpat
```

FIG. 4

Human_cdc25c (SEQ ID NO:19)
```
  1 mstelfsstr eegssgsgps frsnqrkmln lllerdtsft vcpdvprtpv gkflgdsanl
 61 silsggtpkr cldlsnlssg eitatqltts adldetghld ssglqevhla gmnhdqhlmk
121 cspaqllcst pngldrghrk rdamcsssan kendngnlvd semkylgspi ttvpkldknp
181 nlgedqaeei sdelmefslk dqeakvsrsg lyrspsmpen lnrprlkqve kfkdntipdk
241 vkkkyfsgqg klrkglclkk tvslcditit qmleedsnqg hligdfskvc alptvsgkhq
301 dlkyvnpetv aallsgkfqg liekfyvidc rypyeylggh iqgalnlysq eelfnfflkk
361 pivpldtqkr iiivfhcefs sergprmcrc lreedrslnq ypalyypely ilkggyrdff
421 peymelcepq sycpmhhqdh ktellrcrsq skvqegerql reqiallvkd msp
```

FIG. 5

PEPTIDE PROTECTION AGAINST ULTRAVIOLET LIGHT TOXICITY

This application is a Section 371, United States national stage filing of PCT/US2010/057177 filed 18 Nov. 2010 which claims benefit of priority to U.S. 61/262,790 filed 19 Nov. 2009, each of which is herein incorporated by reference in its entirety.

FIELD OF THE INVENTION

The invention relates to peptides having biological and therapeutic activity. Particularly, the invention relates to short peptides that protect against mutagen-induced cellular/tissue toxicity. For example, the inventive peptides protect against toxicity in the skin that occurs after UV light exposure. One function of the inventive peptides is to block the phosphorylation, and therefore activation, of certain cell cycle regulatory proteins. The invention is further related to methods of using the inventive peptides to reduce the level cellular/tissue toxicity following mutagen (e.g., UV light) exposure.

BACKGROUND OF THE INVENTION

When keratinocytes are exposed to DNA damaging elements (mutagens) such as ultraviolet (UV) radiation, cell cycle checkpoints are activated thereby blocking cell division. The arrest of the cell cycle in G2 phase after mutagen-induced damage allows time for DNA repair. However, if the checkpoint process is interrupted or inhibited, then the frequency of cancer-producing events (e.g., DNA mutations) is reduced. This has been demonstrated in vitro and in vivo through the application of caffeine to skin before and after UV irradiation (Lu et al., 2008, Cancer Res. 68:2523-2529; Heffernan et al., 2009, J. Invest. Dermatol. 129:1805-1815). The basis for this phenomenon is that caffeine inhibits the mitotic checkpoint pathway, allowing DNA-damaged cells to proceed to mitosis and die via apoptosis as their DNA is incapable of satisfactory replication. Allowing cell cycle progression despite DNA mutation/damage and the apoptotic cell death that occurs as a result prevents the fixation of mutagen-induced mutations in the affected tissue. This process thereby reduces the number of genetically altered cells that would otherwise have the potential to develop into cancerous lesions such as carcinoma.

The ability of caffeine to reduce the carcinogenic effects of UV light on skin has raised an interest in using this agent in skin care therapeutic and cosmetic skin care applications. However, the use of caffeine in skin care products is problematic given its lack of specificity. Aside from its salutary effects, caffeine can induce undesirable effects in skin (e.g., vasodilation, drying, etc.). Given these drawbacks, other approaches have been sought after for preventing the damaging effects of mutagens in skin and related tissues.

The use of short peptides for the development of skin care products is very popular due to their natural amino acid-based structure, specificity, lack of toxicity, and lack of side effects. These qualities render peptides as a suitable starting point for the development of novel chemopreventive agents for supplementation to skin care compositions. Peptides having chemopreventive and chemotherapeutic properties and that are applicable to protecting skin from the damaging effects of sunlight are described herein.

SUMMARY OF THE INVENTION

An embodiment of the instant invention is directed to a method of reducing the activity of a cell cycle checkpoint kinase. Such a method can comprise exposing a checkpoint kinase to a peptide that is five to nine amino acid residues in length and comprises SEQ ID NO:13. The cell cycle checkpoint kinase in this and other embodiments may be in the activated state. Examples of peptides that can be applied in this or other methods described herein comprise or consist of SEQ ID NO:2, 3, 5, 6, 8, or 10.

Other examples of peptides that can be used in the methods described herein are those having a histidine residue that is directly contiguous with the SEQ ID NO:13 sequence. Other peptides can be amidated at the carboxy terminus thereof. Specific examples of such amidated peptides are those comprising or consisting of SEQ ID NO:2, 3, 5, 6, 8, or 10.

Checkpoint kinases targeted by the disclosed methods may comprise or consist of checkpoint kinase-1 (Chk1) or checkpoint kinase-2 (Chk2). The checkpoint kinase may be activated as a result of DNA damage in a cell. Such DNA damage may be incurred by a mutagenic agent. Examples of mutagenic agents are those that are capable of inducing DNA damage in skin (e.g., ultraviolet radiation). The disclosed methods can also comprise exposing a cdc25 (cell division cycle 25) phosphatase to a peptide described herein; cdc25c is an example of a cdc25c that can be targeted in the instant invention.

Another embodiment of the instant invention is directed to a method of treating the skin of a mammal. Such a method can comprise reducing the activity of a cell cycle checkpoint kinase (e.g., Chk2) in the skin by exposing the checkpoint kinase to a disclosed peptide. Another embodiment of the instant invention is directed to a treating the skin of a mammal by applying a disclosed peptide to the skin.

Another embodiment of the instant invention is directed to a peptide that is five to nine amino acid residues in length and comprises SEQ ID NO:13. Examples of such a peptide comprise or consist of SEQ ID NO:2, 3, 5, 6, 8, or 10. Other examples of peptides of the invention have a histidine residue that is directly contiguous with the SEQ ID NO:13 sequence. Other peptides can be amidated at the carboxy terminus thereof. Specific examples of such amidated peptides are those comprising or consisting of SEQ ID NO:2, 3, 5, 6, 8, or 10.

Another embodiment of the instant invention is directed a composition comprising a peptide of the instant invention and a pharmaceutically acceptable carrier. The composition can be in the form of an aerosol, emulsion, liquid, lotion, cream, paste, ointment, powder, or foam.

BRIEF DESCRIPTION OF THE DRAWINGS

FIG. 1 shows the amino acid sequences of certain inventive peptides (SEQ ID NOs:1-10) as they generally align with each other and SEQ ID NO:11 (human tyrosinase). The underlined residues in certain of the peptides (SEQ ID NOs: 1-7) constitute conservative amino acid substitutions with respect to SEQ ID NO:11.

FIG. 3 shows the amino acid sequence of human Chk2 (SEQ ID NO:17). This sequence is the same as that disclosed at the U.S. National Center for Biotechnological Information (NCBI) website (or GenBank) under accession number AAH04207.

FIG. 4 shows the amino acid sequence of human Chk1 (SEQ ID NO:18). This sequence is the same as that disclosed at the NCBI website (or GenBank) under accession number AAC51736.

FIG. 5 shows the amino acid sequence of human cdc25c (SEQ ID NO:19). This sequence is the same as that disclosed at the NCBI website (or GenBank) under accession number AAR32098.

DETAILED DESCRIPTION OF THE INVENTION

Figure 2:
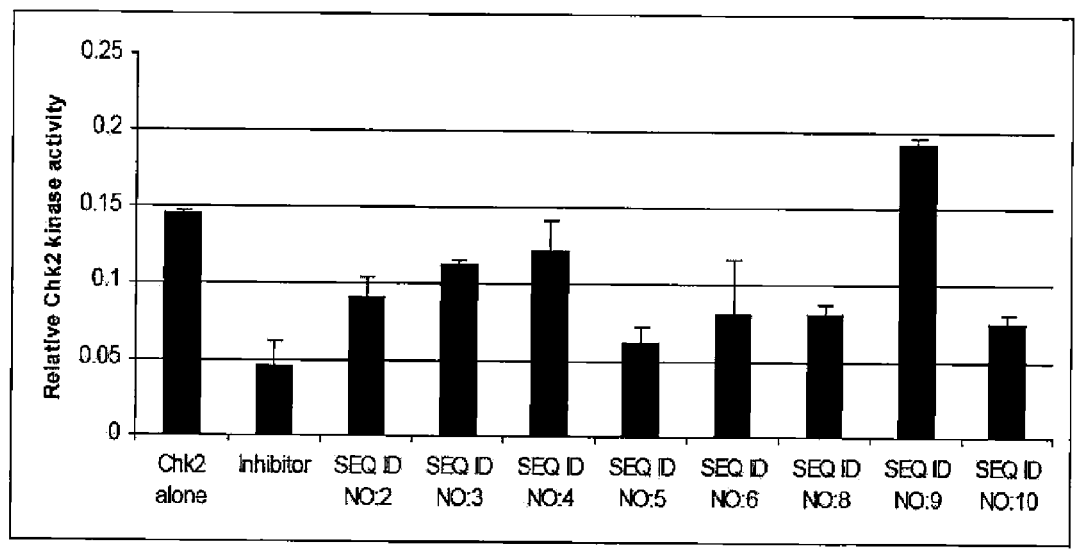
FIG. 2 shows the inhibition of checkpoint kinase 2 (Chk2) activity by staurosporine or certain inventive peptides. Control Chk2 activity is shown with the first bar. The peptides shown in the figure (SEQ ID NOs:2-6 and 8-10) are carboxy-terminal amidated (—$CONH_2$).

The inventive peptides (e.g., those listed in Table 1 and FIG. 1) can comprise L- or D-amino acid enantiomers, either containing residues of one enantiomeric form or a combination of both forms. The peptides may be further augmented or modified as described in the following non-limiting examples, just so long as their primary amino acid sequences are unaltered; in this manner, the peptides consist of a certain amino acid sequence, but may comprise certain modifications. The carboxy-terminus of the peptides can be acidic (—COOH) or be amidated (e.g. —CONH$_2$, —CONHR, or —CONR$_2$). Amidation of the carboxy-terminus may render the inventive peptides less susceptible to protease degradation and increase their solubility compared to their free acid forms, therefore providing heightened therapeutic potency. The peptides may also be lipidated, which may provide for enhanced skin penetration. One or more of the molecular bonds that link the amino acids of each peptide may be a non-peptide bond. Such non-peptide bonds include, but are not limited to, imido, ester hydrazine, semicarbazoide and azo bonds.

TABLE 1

| SEQ ID NO: | Sequence |
|---|---|
| 1 | DYHTLYQTHL |
| 2 | YHSLYQSHL |
| 3 | YHSIYQSHI |
| 4 | DFHSLFQSH |
| 5 | YHSLYESK |
| 6 | FHSIYQSH |
| 7 | FKSLYQS |
| 8 | HSLYQSH |
| 9 | HSLYQS |
| 10 | SLYQS |
| 13 | S-L/I-Y-Q/E-S |
| 14 | SLYQS |
| 15 | SLYES |
| 16 | STYES |

A variety of modifications can be made to the inventive peptides as long as their primary amino acid sequences are retained. Some modifications may be used to increase the potency of the peptide, while other modifications may facilitate peptide handling. Peptide functional groups that may typically be modified include hydroxyl, amino, guanidinium, carboxyl, and amide groups. Typical, non-limiting reactions of these groups include the following: acetylation of hydroxyl groups by alkyl halides; esterification, amidation or hydrogenization (i.e., reduction to alcohol) of carboxyl groups; deamidation, acylation, alkylation, arylation of amino groups (e.g., primary amino group of the peptide or the amino group of lysine residues). SEQ ID NOs:1-10 and/or 13, for example, can be amidated at the carboxy terminus (—CONH$_2$).

The above discussion notwithstanding, the inventive peptides can be designed to have certain amino acid alterations at one or more amino acid residue positions. For example, one, two, or three residues are changed to a conserved residue or residues. Amino acid conservation strategies are well known in the art; for example, it is well known that lysine, phenylalanine, isoleucine, threonine and glutamate can substitute for, respectively, histidine, tyrosine, leucine, serine and glutamine without largely affecting the structure and function of the original peptide. Optionally, the inventive peptide may have one less amino acid compared to any one of SEQ ID NOs:1-10 or 13; or have two less amino acids (adjacent or non-adjacent). Variant forms of the inventive peptide should be at least 80%, 85%, 90%, 95%, 96%, 97%, 98%, or 99% identical with any one of SEQ ID NOs:1-10 or 13. Variant forms of the inventive peptides should have at least 10%, 20%, 30%, 40%, 50%, 60%, 70%, 75%, 80%, 90%, or 95% of the activity or function possessed by any one of SEQ ID NOs:1-10 or 13.

Examples of the activity or function possessed by SEQ ID NOs:1-10 and 13 are chemoprevention of cancer (e.g., carcinoma, sarcoma, melanoma, skin cancer), preventing development of a pre-cancerous cell population in tissue (e.g., skin) exposed to a mutagenic/carcinogenic agent (e.g., UV radiation), blocking cell cycle arrest and DNA repair following exposure of a cell (e.g., a skin cell, keratinocyte, melanocyte, or fibroblast) to a mutagenic/carcinogenic agent (e.g., UV radiation), blocking activation of cdc25c by a DNA damage repair pathway such as that orchestrated through a checkpoint kinase (e.g., checkpoint kinase-2 [Chk2]), blocking or reducing toxicity (such as in skin) related to or induced by exposure to a mutagen/carcinogen (e.g., UV radiation), blocking or reducing the negative effects of a mutagen/carcinogen on characteristics of healthy skin (e.g., tone, elasticity, hydration, coloration, firmness, smoothness). Chemoprevention (chemoprophylaxis) can refer to the use of agents such as the inventive peptides to reduce the risk of, or delay the development or recurrence of, neoplasia (e.g., cancer, pre-cancerous lesions, benign overgrowth lesions). Toxicity in the skin as induced by a mutagenic agent or any other agent (e.g., chemotherapeutic, irritant) can manifest in the form of erythema, alopecia (hair loss), photosensitivity (increased sensitivity to sunlight), recall reactions (e.g., effects of chemotherapy on site previously treated with radiation), acneiform (pimple-like) eruptions, skin necrosis, neutrophilic eccrine hidradenitis, eccrine squamous metaplasia, hyperpigmentation, nail changes, mucositis, sclerotic dermal reactions, vascular injury, xerosis, edema (swelling), urticaria, skin ageing (e.g., thinning, reduced elasticity, wrinkling, sagging, increased pigmentation [e.g., freckling, solar lentigo, guttate hypomelanosis], telangiectases, angioma, purpura, solar comedones, colloid milia, seborrhoeic keratoses), blistering, dermatitis, vegetating/fungating nodules (raised firm lumps), exudative plaques, vegetating or necrotic ulcer with pustules, scarring, panniculitis, ulceration, pain and/or burns. By "reducing," "inhibiting," "blocking," or "preventing" as referred to herein, it is meant that an inventive peptide brings down the occurrence, severity, magnitude, morbidity, or associated symptoms of a condition by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, or 100% compared to how the condition would normally exist without application of the peptide or composition comprising the peptide.

Though the inventive peptides can be produced without the addition of other sequences, the option exists to incorporate the inventive sequences within a larger sequence. For example, an inventive peptide can have extra amino acid residues added to either or both of its N- and C-termini. An example would be a marker epitope such as Flag, which is commonly used to track proteins; marker epitopes well known in the art include myc, His, HA (hemagglutinin), for example. Thus, the present invention covers peptides that either consist of or comprise the inventive peptides. Although the inventive peptides may be provided within a larger sequence (i.e., comprised within), the combination of the inventive peptide sequence with an additional sequence(s) should not constitute any protein or peptide sequence that is naturally expressed by an animal cell (e.g., human cell). Where language is used herein to describe that the peptide "consists" of a sequence, such a peptide, while being limited to a certain contiguous amino acid sequence, may comprise (i.e., be conjugated to) non-amino acid moieties or other peptides/proteins (such peptides/proteins would be conjugated to the inventive peptide via a non-peptide bond).

The peptides of the current invention may be 5, 6, 7, 8, or 9 contiguous amino acids in length and comprise or consist of SEQ ID NO:13 (S-L/I-Y-Q/E-S). Non-limiting examples of such peptides are SEQ ID NOs:2, 3 and 5-10. Other non-limiting examples of such peptides are fragments of SEQ ID NOs:2, 3 and 5-8 that comprise SEQ ID NO:13. Following from the formula of SEQ ID NO:13, other peptides of the current invention may be 5, 6, 7, 8, or 9 contiguous amino acids in length and comprise or consist of SEQ ID NO:14 (S-I-Y-Q-S), SEQ ID NO:15 (S-L-Y-E-S), or SEQ ID NO:16 (S-I-Y-E-S). Other peptides of the current invention may comprise SEQ ID NO:13, wherein a histidine residue is directly contiguous with the SEQ ID NO:13 sequence; examples of such peptides are SEQ ID NOs:2, 3, 5, 6, 8 and 9. Short peptides containing SEQ ID NO:13 are all related with each other on a structural level, given the structural/chemical similarity between leucine and isoleucine (i.e., position 2 of SEQ ID NO:13) and between glutamine and glutamate (i.e., position 4 of SEQ ID NO:13). Other amino acids beside leucine and isoleucine may occupy position 2 of SEQ ID NO:13, such as alanine, valine, glycine, or methionine. Other amino acids beside glutamine and glutamate may occupy position 4 of SEQ ID NO:13, such as asparagine, aspartate, arginine, or lysine.

Alternatively, the peptides of the current invention may be 5, 6, 7, 8, or 9 contiguous amino acids in length and comprise or consist of SEQ ID NO:10 (S-L-Y-Q-S). Non-limiting examples of such peptides are SEQ ID NOs:2 and 7-9. Other non-limiting examples of such peptides are fragments of SEQ ID NOs:2, 7 and 8 that comprise SEQ ID NO:10. Other peptides of the current invention may comprise SEQ ID NO:10, wherein a histidine residue (H) is directly contiguous with the SEQ ID NO:10 sequence; examples of such peptides are SEQ ID NOs:2, 8 and 9.

All of the embodiments of the inventive peptides may be in the "isolated" state. For example, an "isolated" peptide is one that has been completely or partially purified. In some instances, the isolated peptide will be part of a greater composition, buffer system or reagent mix. In other circumstances, the isolated peptide may be purified t homogeneity. A composition may comprise the peptide at a level of at least about 50, 80, 90, or 95% (on a molar basis) of all the other macromolecular species that are also present therein. The inventive peptides may comprise heterologous combinations of components. Mixtures of the inventive peptides may be used in practicing the invention.

The inventive peptides may be conjugated to soluble or insoluble carrier molecules to modify their solubility properties as needed and to increase the local concentrations of peptides in targeted tissues. Examples of soluble carrier molecules include polymers of polyethylene glycol (PEG) and polyvinylpyrrolidone; examples of insoluble polymers include silicates, polystyrene, and cellulose. Peptides may also be micro-encapsulated to enhance their stability during and after therapeutic application; typically, polyester and PEG microspheres are used to encapsulate and stabilize the peptides.

Various methods of preparing microspheres for peptide encapsulation may be employed depending upon the hydrophilic or hydrophobic nature of the peptide composition to be encapsulated. Examples of protocols for such methods are found in Wang et al. (*J. Control. Release* 17:23, 1991) and U.S. Pat. No. 4,324,683, both of which are herein incorporated by reference in their entirety. In vitro peptide release studies may be performed to determine the relative availability of the peptide after incorporation into a microsphere. Microspheres (200 mg) are suspended in 2.5 mL phosphate-buffered saline (PBS, pH 7.2) and agitated at 37 ° C. and 100 rpm in an environmental incubator shaker (G-24, New Brunswick Scientific Co., Edison, N.J.). At specific sampling times (each day for the first 4 days and every other day thereafter) the buffer solution is completely removed and replaced with fresh PBS. The peptide content of the PBS is measured using the Bradford method or other suitable quantitative assay typically used for protein analysis.

The following procedures and parameters are provided for guidance purposes only and are all well known to those skilled in the art. All the disclosed peptides may be synthesized using standard Fmoc (9-fluorenylmethoxycarbonyl) solid-phase chemistry on an Advanced ChemTech APEX 396 Multiple Peptide Synthesizer. The synthesizer is equipped with a 40-well reaction block for the production of up to 40 peptides simultaneously at a scale of 0.15 mmol. The peptides can be prepared as either amidated or free acid sequences using standard amino acids. The resin is first washed and pre-swelled with N,N-dimethyl formamide (DMF). The swelling time is one hour for Rink amide resins. The Fmoc protecting group is removed with 25% piperidine in DMF for 25 minutes, after which the piperidine is completely washed from the resin. To control racemization processes, the Fmoc amino acid monomers are pre-activated in an equimolar solution of 1-hydroxy-benzotriazole (HOBt) or 1-hydroxy-7-aza-benzotriazole (HOAt) in 0.5 M DMF. The amide couplings are carried out using O-(7-azabenzotriazol-1-yl)-1,1,3,3-tetramethyluronium hexafluorophosphate (HATU) or 2-(1H-benzotriazol-1-yl-)-1,1,3,3-tetrameth-yluronium hexafluorophosphate (HBTU) as an activation agent and 2.5-5.0 fold molar excess of amino acid under basic conditions using a hindered base (diisopropylethylamine). The coupling times are 1-1.5 hours followed by a wash and re-coupling to accomplish a double or triple couple before deprotection and continuation of the growing peptide chain. Coupling efficiency is monitored using the standard Kaiser test. Once peptide synthesis is completed on the resin, the final Fmoc group is removed as above and the sequences are left as the free base form.

Cleavage of the acid-labile linkage of the peptide to the resin is accomplished using 95% trifluoroacetic acid (TFA) and water with the appropriate scavengers added. After cleavage is allowed to proceed for about 30 minutes to one hour, the released peptides are immediately removed from the cleavage block and transferred to tubes for the removal of the TFA under reduced pressure. The peptides are then ready for purification and analysis via high performance liquid chromatography (HPLC) using a reverse phase C18 column and mass spectrometry. Primary sequence confirmation and preparative purification are accomplished using an LC/MS/MS system (ABI API2000).

General to the above protocol, the peptides may be produced using any method known to those skilled in the art such as those disclosed in Merrifield (*J Am Chem Soc.* 85:2149, 1963); Carpino et al. (*J Org Chem.* 51:3732, 1986); Merrifield et al. (*Anal Chem.* 38:1905, 1966); or Kent et al. [*High Yield Chemical Synthesis Of Biologically Active Peptides On An Automated Peptide Synthesizer Of Novel Design*, IN: PEPTIDES 1984 (Ragnarsson, ed.) Almqvist and Wiksell Int., Stockholm (Sweden), pp. 185-188], all of which are herein incorporated by reference in their entirety. The peptides can be produced by a machine capable of sequential addition of amino acids to a growing peptide chain. However, the peptides may also be manufactured using standard solution phase methodology, which can be amenable to large-scale production efforts.

Additional embodiments of the current invention are directed towards methods of using the above-described peptides, such as in formulations or as therapeutic agents. These methods may involve the use of a single peptide, or multiple peptides in combination (i.e., a mixture).

In certain instances, the inventive composition can be disposed within devices placed upon, in, or under the skin. Such devices include transdermal patches, implants, and injections which release the substances in such a manner as to contact the skin or hair follicle either by passive or active release mechanisms. The substance can be applied, for example, topically to the epidermis at regular intervals, such as once or twice daily, in a suitable vehicle and at an effective concentration. One or more injections to the skin offer another route for administering the inventive peptides to the skin or any other tissue.

The compositions used to deliver the peptides in the methods described herein can be in the form of an aerosol, emulsion, liquid, lotion, cream, paste, ointment, powder, foam, or other pharmaceutically acceptable formulation. Furthermore, the peptides can be delivered using less involved formulations such as deionized/distilled water, PBS or standard medical saline solutions. Generally, a pharmaceutically acceptable formulation would include any carrier suitable for use on human skin or mucosal surface. Such pharmaceutically acceptable carriers include ethanol, dimethyl sulfoxide, glycerol, silica, alumina, starch, and equivalent carriers and diluents. The formulation may optionally have cosmetic appeal, and/or contain other agents such as retinoids or other peptides that can act as adjuvants for the therapeutic action of the inventive peptides. Antibiotics can also be added to the formulation in order to ward off infection, thereby permitting maximal healing processes to occur. The concentration of the peptide in the composition can be about 0.1 µg/mL to about 50 µg/mL or about 0.1 µg/mL to about 20 µg/mL; however, the ultimate concentration employed may vary outside these ranges, depending on the nature of the target tissue, the bioactivity of the inventive peptide and the use of any adjuvant or technique to obtain enhanced composition absorption. Such determinations are well within the normal skill in the art. For example, the concentration of the peptide(s) used in practicing the instant invention can be about 0.1, 1, 2, 5, 10, 15, 20, 25, 50, 75, 100, 200, 500, or 1000 µg/mL.

The administration of the inventive peptides and associated compositions may be made to humans and animals, including all mammals (e.g., pigs, cows, horses, sheep, goats, mice, rats, cats, dogs, ferrets, primates). Application may also be made in combination with typical and/or experimental materials such as tissue grafts, tissue culture products, oxygen and dressings. In general, the composition can be administered topically, orally, transdermally, systemically, or by any other method known to those of skill in the art to be useful to deliver the inventive peptides to the target tissue. Compositions may also be applied in an in vitro or ex vivo manner, either to cells or patient grafts growing in culture, for example.

Due to their small size, the peptides are expected to be able to gain by themselves a level of permeability through the skin; however, certain techniques may be used to amplify this movement. For example, lipophilic (non-polar) groups can be added to the peptides, or the peptides can be delivered to the skin in a lipophilic excipient, in order to enhance peptide accessibility to the stratum corneum to allow translocation to the lower epidermal layers. In this manner such lipophilic modifications may be considered as having a pro-drug effect. Permeation enhancers such as known solvents and surfactants may be used in the excipient to allow better peptide absorption. Special techniques that are anticipated to be useful in enhancing peptide access to the targeted tissue/injury include, injection regimens, iontophoresis, electrophoresis and ultrasound. An iontophoretic device consists of two electrodes immersed in an electrolyte solution and placed on the skin. When an electric current is applied across the electrodes, an electric field is created across the stratum corneum that drives the delivery of the peptides. Electroporation involves the application of high-voltage electric pulses to increase the permeation through lipid bilayers. This differs from iontophoresis in the duration and intensity of the application of electrical current (iontophoresis uses a relatively constant low-voltage electric field). The high-voltage electric pulse of electroporation is believed to induce a reversible formation of hydrophilic pores in the lipid lamellae membranes that can provide a high degree of permeation enhancement. Ultrasound applies sound waves having a frequency greater than 16 kHz to the skin, which causes compression and expansion of the tissue through which the sound waves travel. The resulting pressure variations cause a number of processes (e.g., cavitation, mixing, increase in temperature) that may enhance permeation of the peptides.

The instant invention can comprise one or more protease inhibitors. A protease inhibitor can be selected to specifically target proteases that would be expected to degrade the selected bioactive peptide; such a selection would be determined based on the length and/or sequence of the bioactive peptide. However, protease inhibitors need not necessarily be selected in any specific manner; for example, a protease inhibitor cocktail, which contains two or more inhibitors, can be employed in the instant invention. With certain embodiments of the invention, the protease inhibitor is not one that is specific to inhibiting a virus. The following types of protease inhibitors can be incorporated in the invention: serine protease inhibitors, cysteine protease inhibitors, aspartate protease inhibitors, metalloproteinase inhibitors, thiol protease inhibitors and threonine protease inhibitors Protease inhibitors are well known in the art. Non-limiting examples of protease inhibitors that can be incorporated in the present invention include acetyl-pepstatin, AEBSF (4-[2-Aminoethyl]benzenesulfonyl fluoride) hydrochloride, ALLM (N-Acetyl-Leu-Leu-Met), ALLN (N-Acetyl-Leu-Leu-Nle-CHO), amastatin (*Streptomyces* sp.), ε-amino-n-caproic acid, aminopeptidase N inhibitor, $\alpha_1$-antichymotrypsin, antipain (hydrochloride or dihydrochloride), α2-antiplasmin, antithrombin III, α1-antitrypsin, p-APMSF hydrochloride, aprotinin (e.g., from bovine lung), ATBI (an 11-residue peptide), benzaniidine hydrochloride, bestatin, bestatin methyl ester, calpastatin, calpeptin, carboxypeptidase inhibitor, caspase inhibitor, cathepsin B inhibitor II, cathepsin G inhibitor I, cathepsin inhibitor II, cathepsin inhibitor III, cathepsin inhibitor I, cathepsin K inhibitor I, cathepsin K inhibitor II, cathepsin K inhibitor III, cathepsin L inhibitor I, cathepsin L inhibitor II, cathepsin L inhibitor IV, cathepsin L inhibitor V, cathepsin L inhibitor VI, cathepsin S inhibitor, cathepsin/subtilisin inhibitor, chymostatin, chymotrypsin inhibitor I, cystatin, 1,5-dansyl-glu-gly-arg chloromethyl ketone dihydrochloride, 3,4-dichloroisocoumarin, diisopropylfluorophosphate, dipeptidylpeptidase II inhibitor, dipeptidylpeptidase IV inhibitor I, dipeptidylpeptidase IV inhibitor II, E-64 protease inhibitor, ecotin, EDTA disodium salt dihydrate, EDTA tetrasodium salt, EGTA, elastase inhibitor I, elastase inhibitor II, elastase inhibitor III, elastatinal, 6-amidino-2-naphthyl-4-guanidinobenzoate dimethanesulfonate, glu-gly-arg-chloromethyl ketone, 2-guanidinoethylmercaptosuccinic acid, hexadecylsulfonyl fluoride, α-iodoacetamide, kininogen, leuhistin, leupeptin hemisulfate, $α_2$-macroglobulin, DL-2-mercaptomethyl-3-guanidinoethylthiopropanoic acid, pepstatin A, phenylmethylsulfonyl fluoride, phosphoramidon Disodium Salt, PPack II trifluoroacetate salt, PPack dihydrochloride, prolyl endopeptidase inhibitor II, Na-tosyl-lys chloromethyl ketone hydrochloride, Na-tosyl-phe chloromethyl ketone, tripeptidylpeptidase II inhibitor, trypsin inhibitor (from corn or soybean), D-val-phe-lys chloromethyl ketone dihydrochloride, 1,3-di-(N-carboxybenzoyl-L-leucyl-L-leucyl)amino acetone, o-phenanthroline, ursolic acid (e.g., Rosemary extract), tranexamic acid (4-[aminomethyl]cyclohexane-1-carboxylic acid) (clinically marketed as Cyklokapron in the U.S. and as Transamin in Asia), Fmoc-Lys (Boc), Fmoc-Arg(Pmc), benzoyl-Arg-nitroanilide, benzoyl-Arg-naphthylamide, and α-2-macroglobuline.

The protease inhibitor used in the invention may be a peptide or protein, such as an enzyme. Non-limiting examples of such inhibitors are the serpins, which include alpha-1-antitrypsin, complement 1-inhibitor, antithrombin, alpha-1-antichymotrypsin, plasminogen activator inhibitor 1, and neuroserpin.

Components that are typically incorporated into skin care preparations are well known in the art. Beside the bioactive peptide component, the instant invention can contain other active agents such as niacinamide, phytantriol, farnesol, bisabolol and salicylic acid. It is expected that certain additional active agents will act synergistically with the bioactive peptide component, or will enhance the shelf-life of the formulation.

Where the composition is to be in contact with animal or human skin, additional components should be chosen that are suitable for application to keratinous tissue (i.e., stabile, low toxicity, hypoallergenic). The CTFA Cosmetic Ingredient Handbook, Second Edition (1992), which is herein incorporated by reference in its entirety, describes a wide variety of non-limiting cosmetic and pharmaceutical ingredients commonly used in the skin care industry that are suitable for use in the compositions of the present invention. Examples of these ingredient include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, benzoyl peroxide, erythromycin, zinc), anti-caking agents, antifoaming agents, antimicrobial agents (e.g., iodopropyl butylcarbamate), antioxidants, binders, biological additives, buffering agents, bulking agents, chelating agents, chemical additives, denaturants, external analgesics, polymers (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid [vitamin C], magnesium ascorbyl phosphate, ascorbyl glucosamine), skin-conditioning agents (e.g., humectants, including miscellaneous and occlusive), skin soothing and/or healing agents (e.g., panthenol and derivatives [e.g., ethyl panthenol], aloe vera, pantothenic acid and its derivatives, allantoin, bisabolol, dipotassium glycyrrhizinate), thickeners, particulate materials, structuring agents and vitamins. Many of these agents are described in detail in U.S. Pat. No. 6,492,326, which is herein incorporated by reference in its entirety, specifically with respect to the various ingredient descriptions.

The compositions of the present invention may contain a particulate material such as a metallic oxide. These particulates can be coated or uncoated, charged or uncharged. Non-limiting examples of particulate materials useful for preparing the instant invention include bismuth oxychloride, iron oxide, mica, mica treated with barium sulfate and $TiO_2$, silica, nylon, polyethylene, talc, styrene, polypropylene, ethylene/acrylic acid copolymer, sericite, aluminum oxide, silicone resin, barium sulfate, calcium carbonate, cellulose acetate, titanium dioxide, polymethyl methacrylate, and mixtures thereof. Inorganic particulate materials such as $TiO_2$, ZnO (zinc oxide), or $ZrO_2$ are commercially available from a number of sources. Particulate materials can be present in the composition at levels of from 0.01% to 2% by weight, or from 0.05% to 1.5% by weight, or from 0.1% to 1% by weight (all measures approximate).

The compositions of the present invention may contain a conditioning agent selected from humectants, moisturizers, or skin conditioners. A variety of these materials can be employed and each can be present at a level of from about 0.01% to 20%, or from about 0.1% to 10%, or from about 0.5% to 7% by weight of the composition (all measures approximate). These materials include, but are not limited to, guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol and hexylene glycol; polyethylene glycols; sugars (e.g., melibiose) and starches; sugar and starch derivatives (e.g., alkoxylated glucose, fructose, glucosamine); hyaluronic acid; lactamide monoethanolamine; acetamide monoethanolamine; panthenol; allantoin; petroleum jelly; and mixtures thereof.

The compositions of the present invention can contain a structuring agent, which can be used for preparing a oil-in-water emulsion. Without being limited by any theory, it is believed that the structuring agent assists in providing rheological characteristics to the composition which contribute to the stability of the composition. For example, the structuring agent tends to assist in the formation of liquid crystalline gel network structures. The structuring agent may also function as an emulsifier or surfactant. The instant invention may contain from about 0.1% to 20%, from about 0.1% to 10%, or from about 0.5% to 9% of one or more structuring agents by weight of the composition (all measures approximate).

Structuring agents than can be incorporated in the present invention are selected from stearic acid, palmitic acid, stearyl alcohol, cetyl alcohol, behenyl alcohol, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. Other structuring agents that can be used in the present invention are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof.

Additional features, modes of production and use of the inventive peptides are described, for example, in U.S. Pat. Nos. 6,974,799 and 5,492,894. Both these patents are incorporated herein by reference in their entirety.

Methods

The instant invention can also drawn to a method of inhibiting or preventing neoplastic growth in a tissue of a mammal by administering peptides described herein. While not being held to any particular mechanism of action, the anti-neoplastic activity of the disclosed peptides is associated with the ability to inhibit the activity of cell cycle checkpoint kinases such as checkpoint kinase-2 (Chk2). Inhibiting Chk proteins, which are activated after a cell suffers DNA damage, prevents cells from entering cell cycle arrest, during which time DNA repair occurs. While DNA repair can return sequences back to their original state (i.e., non-mutated), it is usually insufficient to do so with large genetic insults. With the latter situation, the repair process oftentimes fixes (makes permanent) genetic alterations that can contribute to oncogenic processes (e.g., activation of an oncogene, inactivation of a tumor suppressor or gatekeeper gene). By blocking or reducing cell cycle arrest through the inhibition of Chk protein activity, cells can continue to the mitotic phase during which, due to the disruptive effects of certain DNA damage events (e.g., DNA double-strand breaks) on the division process, apoptosis is induced. DNA damage can also be referred to as genotoxic stress. Apoptosis therefore clears out cells carrying deleterious genetic changes; such cells would potentially survive and serve as precursors for neoplastic development if cell cycle arrest is permitted to fully activate thereby allowing for DNA "repair" to occur. In this manner, the instant invention can be used to reduce the accumulation of mutations in a tissue due to the effects of DNA-damaging agents.

The neoplastic growth prevented, inhibited, or treated by the inventive peptides can be benign, pre-cancerous, or cancerous (i.e., malignant). For this reason the disclosed peptides may be considered to have chemopreventive, chemoprophylactic, anti-cancer, anti-neoplastic, anti-carcinogenic, or chemotherapeutic activity. With respect to preventing or inhibiting a neoplastic growth or lesion in a tissue, one or more peptides can be administered to the tissue that otherwise shows no obvious (macroscopic) signs of neoplasia. For example, the peptides can be administered to a healthy tissue before the occurrence of a mutagenic insult (e.g., within 1, 2, 3, 4, 8, 12, 16, 20, 24, 48, 72, 96, or 120 hours pre-insult) (e.g., applied topically to the skin before sun exposure), or shortly after suffering a mutagenic insult (e.g., within 1, 2, 3, 4, 8, 12, 16, 20, 24, 48, 72, 96, or 120 hours post-insult) (e.g., applied topically to the skin before sun exposure). With regard to skin care, the peptides can be applied in either a sunscreen or after-sun preparation. The peptides can also be used to prevent or inhibit the increase in mutations in a tissue, whether it is completely healthy or contains small benign and/or pre-cancerous lesions. Such use can prevent or inhibit the transition of a benign or pre-cancerous lesion into a cancerous/malignant lesion (i.e., prevent or inhibit tumorigenesis), and can thus be said to treat the benign or pre-cancerous lesion. In another aspect, the instant invention can be used to prevent or inhibit hyperplasia in the skin or other tissue.

Examples of benign and/or pre-cancerous neoplastic skin lesions that are prevented or inhibited in their occurrence by the instant invention, or treated, are dermatofibromas, epidermal cysts, hemangiomas, port-wine stains, lymphangiomas, pyogenic granulomas, spider angiomas (nevus araneus), keloids, keratoacanthomas, lipomas, moles, dysplastic nevus, seborrheic keratoses, skin tags, sebaceous hyperplasia, psoriasis and actinic keratosis (solar keratosis). Examples of malignant skin lesions/tumors in skin (i.e., skin cancer) that are prevented or inhibited in their occurrence by the instant invention, or treated, are basal cell carcinoma (e.g., nodular basal cell carcinoma, cystic basal cell carcinoma, cicatricial basal cell carcinoma, infiltrative basal cell carcinoma, micronodular basal cell carcinoma, superficial basal cell carcinoma, pigmented basal cell carcinoma, rodent ulcer [Jacobi ulcer], fibroepithelioma of Pinkus, polypoid basal cell carcinoma, pore-like basal cell carcinoma, aberrant basal cell carcinoma), squamous cell carcinoma (e.g., adenoid squamous cell carcinoma [pseudoglandular squamous cell carcinoma], clear cell squamous cell carcinoma, spindle cell squamous cell carcinoma, signet-ring cell squamous cell carcinoma, basaloid squamous cell carcinoma, verrucous carcinoma, keratoacanthoma), melanoma (e.g., lentigo maligna melanoma, superficially spreading melanoma, acral lentiginous melanoma, mucosal melanoma, nodular melanoma, polypoid melanoma, desmoplastic melanoma, amelanotic melanoma, soft-tissue melanoma, uveal melanoma), dermatofibrosarcoma protuberans, Merkel cell carcinoma, Kaposi's sarcoma, keratoacanthoma, spindle cell tumors, sebaceous carcinomas, microcystic adnexal carcinoma, atypical fibroxanthoma, leimyosarcoma, and angiosarcoma.

Accordingly, the instant invention prevents, inhibits, or treats the development and/or progression of neoplasms in the skin for which the affected cell (i.e., cell type giving rise to the neoplasm) is an epithelial cell, a mesenchymal cell, a keratinocyte, a fibroblast, a melanocyte, a skin stem cell, or a skin progenitor cell. The tissues of the skin targeted by the instant invention are the epidermis, which comprises the stratum basale layer, stratum spinosum layer, stratum granulosum, layer, stratum licidum layer and stratum corneum layer; the dermis, which comprises the papillary and reticular layers; and the subcutaneous tissue, which comprises fat tissue, connective tissue, nerve tissue and blood vessels. All of the aforementioned tissues, layers and cell types are targeted by the instant invention.

Other examples of benign and/or pre-cancerous neoplastic lesions or growth profiles that are prevented or inhibited in their occurrence by the instant invention, or treated, are hyperplasia, dysplasia and metaplasia. Other examples of cancerous neoplastic lesions that are prevented, inhibited, or treated by the instant invention are lung cancer, bone cancer, pancreatic cancer, gastric, head or neck cancer, uterine cancer, ovarian cancer, gynecological cancer, rectal cancer, stomach cancer, colon cancer, breast cancer, uterine cancer, carcinoma of the fallopian tubes, endometrial cancer, cervical cancer, vaginal cancer, vulvar cancer, Hodgkin's Disease, esophageal cancer, cancer of the small intestine, colon cancer, cancer of the endocrine system, cancer of the thyroid gland, cancer of the parathyroid gland, cancer of the adrenal gland, sarcoma of soft tissue, urethral cancer, penile cancer, prostate cancer, chronic or acute leukemia, lymphocytic lymphomas, bladder cancer, kidney or ureter cancer, renal cell carcinoma, carcinoma of the renal pelvis, neoplasms of the central nervous system (CNS), primary CNS lymphoma, spinal axis tumors, brain cancer, pituitary adenoma, hemangioma, glioma, or blastoma.

The instant invention can be practiced as a cosmetic or in the cosmetic treatment of skin. Accordingly, the instant invention acts to maintain normal, healthy skin traits, such as tone, elasticity, hydration, coloration, firmness and smoothness. All of these qualities can degrade with an increase in the amount of damaged cells in the skin, such damaged cells resulting from the effects of mutagens and/or the accumulation of mutations in the skin. Accordingly, the instant invention can prevent, inhibit or treat the effects of aging of the skin; photoaging is one example, where the skin ages partly as a function of degree of UV radiation exposure. The effects of photoaging targeted by the invention are wrinkles, mottling and/or hyperpigmentation, rough or leathery skin, droopiness/sagging, yellowing, dryness and various neoplasms, for example.

Tissues that can be targeted in practicing the instant invention are the skin and associated mucosal tissues of the skin. An associated mucosal tissue of the skin is any tissue organized in a manner similar to the skin, contains epithelial cells, and is directly continuous with the skin. Examples of such tissues are oral, nasopharyngeal, aural, anal and urogenital surfaces, as well as the palpebral conjunctiva of the eye. Other tissues that can be targeted in practicing the instant invention are those derived from the ectoderm, mesoderm and endoderm, or comprise epithelial cells, mesenchymal cells (e.g., fibroblasts), muscle cells, or nerve cells (e.g., neurons). Other organs, organ systems and tissues targeted by the invention are, for example, the circulatory system (e.g., heart, blood, blood vessels), digestive system (e.g., salivary glands, esophagus, stomach, liver, gallbladder, pancreas, small and large intestines, rectum), endocrine system (e.g., hypothalamus, pituitary gland, pineal gland, thyroid, parathyroids, adrenal glands), integumentary system (e.g., skin, hair, nails), lymphatic system (e.g., lymph nodes and vessels), immune system (e.g., tonsils, adenoids, thymus, spleen), muscular system (e.g., cardiac muscle, smooth muscle, skeletal muscle), nervous system (e.g., brain, spinal cord, peripheral nerves, nerves), reproductive system (e.g., ovaries, fallopian tubes, uterus, vagina, mammary glands, testes, vas deferens, seminal vesicles, prostate, penis), respiratory system (e.g., pharynx, larynx, trachea, bronchi, lungs, diaphragm), skeletal system (e.g., bones, cartilage, ligaments, tendons), and excretory system (e.g., kidneys, ureters, bladder, urethra).

As used in practicing the instant invention, the disclosed peptides can act to limit the occurrence of neoplasia (e.g., hyperplasia) by reducing the accumulation of mutations in a tissue resulting from exposure to mutagens of endogenous or ectopic (environmental) origin. The mutagen exposure time may be either acute or chronic. In general, the instant invention can be geared toward blocking mutation accumulation as a result of ectopic mutagen/carcinogen exposure. Examples of ectopic mutagens as discussed herein (i.e., those that originate from outside an animal from the surrounding environment) are ultraviolet (UV) radiation (i.e., UV light) (UV-A, UV-B, UV-C), ionizing radiation (e.g., X-rays, gamma rays, alpha particles), base analogs (e.g., 5-bromouracil), deaminating agents (e.g., nitrous acid [nitrite]), nitroamines, intercalating agents (e.g., ethidium bromide, proflavine, daunomycin, doxorubicin [adriamycin], thalidomide, dactinomycin, aflatoxins, acridine), alkylating agents (e.g., ethylnitrosourea), bromine, heat, sodium azide, psoralen, benzene, benzo-pyrenes, arsenic, asbestos, cadmium, chromium, ethylene oxide, nickel, radon, vinyl chloride, lead and viruses. Examples of endogenous mutagens are 5-methylcytosine, reactive oxygen species (E.G., nitric oxide, superoxide) and transposons. The instant invention is also directed to blocking the accumulation of mutations in a tissue that can result from application of certain irritants. For example, irritants can spur conditions of chronic inflammation, which can lead to cancer formation in various tissues.

Other chemopreventive and/or anticancer agents may be administered with the disclosed peptides in practicing the instant invention. Such administration may include a disclosed peptide and another chemopreventive agent together in the same composition, or involve a scheme where the peptide and agent are applied at different time points during the treatment/prevention regimen. Using both a disclosed peptide and another chemopreventive agent can create synergistic chemopreventive activity. Examples of chemopreventive and/or anticancer agents that can be used in conjunction with the present invention are phytochemicals, caffeine, caffeic acid, genistein, resveratrol, diallyl sulfide, S-allyl cysteine, allicin, lycopene, capsaicin, curcumin, 6-gingerol, ellagic acid, ursolic acid, silymarin, anethol, catechins, emodin, sulforaphane, eugenol, isoleugenol, beta-carotene, oleandarin, polyphenols, indoles (e.g., di-indolylmethane, indole-3-carbinol), isothiocyanates (e.g., phenethylisothiocyanate), non-steroidal anti-inflammatory agents (NSAIDS) (e.g., celecoxib, ibuprofen, sulindac, aspirin), PPAR-gamma agonists (e.g., pioglitazone, rosiglitazone), resiquimod, imiquimod, retinoids (e.g., all-trans-retinoic acid, 9-cis- or 13-cis-retinoic acid, 4-hydroxyretinamide, bexarotene, tararotene, selenium, soy isoflavones, statins (e.g., atorvastatin), sulfur containing antioxidants and vitamin D analogs (e.g., ergocalciferol, cholecalciferol).

One aim for inflicting DNA damage in cancer cells using certain chemotherapeutics or other agents (e.g., gamma-irradiation) is to induce cancer cells to undergo apoptosis thereby effecting tumor regression. However, induction of cell cycle arrest in response to DNA damage can depress this desired outcome. Therefore, another aspect of the instant invention is using the disclosed peptides in combination with a DNA-damaging agent to treat cancer (e.g., a skin cancer) or any other type of neoplasm. A basis for this method is the ability of the disclosed peptides to sensitize DNA-damaged cells to apoptosis (i.e., stimulate cells to undergo apoptosis instead of cell cycle arrest, which allows cancer cell survival) as discussed below. DNA-damaging agents that can be used in practicing the instant invention are, for example, alkylating agents, cisplatin, carboplatin, oxaliplatin, mechlorethamine, cyclophosphamide, chlorambucil, nitrogen mustards, mechlorethamine, ifosfamide, melphalan, nitrosoureas, streptozocin, carmustine (BCNU), lomustine, alkyl sulfonates, busulfan, bendamustine, triazines, dacarbazine (DTIC), temozolomide, ethylenimines, thiotepa, altretamine, hexamethylmelamine, antimetabolites, 6-mercaptopurine, dacarbazine, fludarabine, 5-fluorouracil (5-FU), capecitabine, methotrexate, gemcitabine, cytarabine, pemetrexed, arabinosylcytosine, decitabine, anti-tumor antibiotics, anthracyclines, daunorubicin, doxorubicin (e.g., Adriamycin®), epirubicin, idarubicin, actinomycin-D, bleomycin, mitomycin-C, neocarzinostatin, mitoxantrone, topoisomerase inhibitors, topoisomerase I inhibitors, topotecan, irinotecan, topoisomerase II inhibitors, etoposide, teniposide, plant alkaloids, taxanes, paclitaxel, docetaxel, epothilones, ixabepilone, vinca alkaloids, vinblastine, vincristine, vinorelbine, estramustine, radiation, gamma rays, X-rays and UV radiation. One or more of these agents may be applied to the lesion in combination with a disclosed peptide, or alternatively, a scheme can be practiced where the peptide and DNA-damaging agent are applied at different time points during the treatment regimen.

An aspect of the instant invention is the inhibition of checkpoint kinase (Chk) activity. For example, the invention is directed to inhibiting Chk2 that has been activated by DNA damage in a mammalian cell such as a skin cell. Such DNA damage and/or Chk activity may, for example, be induced in a cell via exposure to UV radiation or any other mutagen present in the environment. DNA damage induced by UV light generally comprises cyclobutane pyrimidine dimers and 6-4 pyrimidine-pyrimidone products. While not being held to any particular theory or mechanism, Chk is inhibited by the ability of the disclosed peptides to block or downregulate/down-modulate its inhibitory kinase activity toward cdc25 (cell division cycle 25) phosphatases such as cdc25c. Under normal cell conditions (little or no DNA damage), cdc25c sets off a signal cascade leading to mitosis, but under DNA damage conditions, activated Chk inhibits cdc25c. Therefore, blocking Chk activity increases the chances that cdc25c will be capable of signaling for mitosis, even under conditions of DNA damage which would normally (i.e., when Chk in not inhibited) downregulate cdc25c. DNA-damaged cells that are allowed entry to mitosis are later cleared by apoptosis, given the incompatibility of DNA damage with normal mitotic processes. Accordingly, an aspect of the instant invention is directed to inducing the clearance of DNA-damaged cells via apoptosis. Another aspect of the instant invention is directed to inhibiting cell cycle arrest that normally occurs in response to DNA damage.

Examples of the Chk enzymes targeted by the instant invention are Chk1 and Chk2, both of which are well known in the art. These serine/threonine kinases are structurally and functionally conserved across eukaryotic species, the human versions of which phosphorylate human cdc25c phosphatase at serine-216 (or the equivalent serine residue, depending on where the Chk-targeted sequence is within a cdc25c variant [e.g., splice variant]). A method of using the inventive peptides to inhibit Chk1- and/or Chk2-mediated phosphorylation of cdc25c (e.g., at the serine-216 position or equivalent serine residue) is part of the instant invention. The instant invention can target the Chk proteins as they naturally exist in cells in vivo.

Activated Chk enzymes (such as they exist in response to DNA damage) can be activated by being phosphorylated by upstream factors (e.g., ATM [ataxia telangiectasia-mutated protein], ATR [ATM-RAD3-related protein]) in DNA damage-sensing pathways or via autophosphorylation. Non-activated forms of Chk may have little or no kinase activity compared to activated forms of Chk. Activated Chk enzymes can phosphorylate cdc25c, for example. Example Chk2 phosporylation sites that can activate this enzyme are at the threonine-26, serine-50, threonine-68, threonine-383 and/or threonine-387 residue positions (or equivalent positions thereof within a Chk2 variant [e.g., splice variant]). Example Chk1 phosporylation sites that can activate this enzyme are at the serine-286, serine-301, serine-317 and/or serine-345 residue positions (or equivalent positions thereof within a Chk1 variant [e.g., splice variant]).

Chk2, which is encoded by the CHEK2 gene in humans, has an amino acid sequence as shown in FIG. 3 (SEQ ID NO:17). Human Chk2 is also known in the art as "CHK2 checkpoint homolog (S. pombe)," CDS1, and Rad53. SEQ ID NO:17 is presented for reference purposes only, since human Chk2 and other mammalian Chk2 protein sequences are known. For example, the U.S. National Center for Biotechnological Information (NCBI) website (or GenBank) discloses human Chk2 amino acid sequences under accession numbers AAH04207, BAB17231, NP_009125, NP_001005735, NP_665861, O96017, AAS58460, AAD48504, AAC83693, EAW59757, EAW59756, EAW59754, CAX11959, CAX11958, CAX11957, CAX14028, CAX14027, CAX14026, CAH73823, CAH73875, AAV41895 and BAF83443, all of which sequences are herein incorporated by reference in their entirety. For purposes of practicing the instant invention, Chk2 may comprise or consist of an amino acid sequence that is at least about 50%, 60%, 70%, 75%, 80%, 85%, 90%, 91%, 92%, 93%, 94%, 95%, 96%, 97%, 98%, or 99% identical to SEQ ID NO:17.

Chk1, which is encoded by the CHEK1 gene in humans, has an amino acid sequence as shown in FIG. 4 (SEQ ID NO:18). Human Chk1 is also known in the art as "CHK1 checkpoint homolog (S. pombe)." SEQ ID NO:18 is presented for reference purposes only, since human Chk1 and other mammalian Chk1 protein sequences are known. For example, the NCBI website (or GenBank) discloses human Chk1 amino acid sequences under accession numbers AAC51736, AAW02681, AAH04202, BAF85238, BAA84577, CAB70558, O14757, AAM58752, AAM78553, CAD10662, AAH17575, AAE84492, CAZ65679, AAB88852, ABM83833, ABM87141, AAE67465, AAE67917, AAX36253, BA145672, NP_001107594 and NP_001265, all of which sequences are herein incorporated by reference in their entirety. For purposes of practicing the instant invention, Chk1 may comprise or consist of an amino acid sequence that is at least about 50%, 60%, 70%, 75%, 80%, 85%, 90%, 91%, 92%, 93%, 94%, 95%, 96%, 97%, 98%, or 99% identical to SEQ ID NO:18.

cdc25c (cell division cycle 25C), which is a tyrosine phosphatase, is encoded by the CDC25C gene in humans and has an amino acid sequence as shown in FIG. 5 (SEQ ID NO:19). Human cdc25c is also known in the art as "M-phase inducer phosphatase 3" and "cell division cycle 25 homolog C (S. pombe)." SEQ ID NO:19 is presented for reference purposes only, since human cdc25c and other mammalian cdc25c protein sequences are known. For example, the NCBI website (or GenBank) discloses human cdc25c amino acid sequences under accession numbers AAR32098, P30307, NP_001781, AAX36531, EAW62145, EAW62149, AAX29802, AAX29802, ABP29523, EAW62148, BAG63273, AAA75741, AAE74714, AAH19089 and AAA35666, all of which sequences are herein incorporated by reference in their entirety. For purposes of practicing the instant invention, cdc25c may comprise or consist of an amino acid sequence that is at least about 50%, 60%, 70%, 75%, 80%, 85%, 90%, 91%, 92%, 93%, 94%, 95%, 96%, 97%, 98%, or 99% identical to SEQ ID NO:19.

While one aspect of the instant invention is drawn to blocking the downregulatory activity of activated Chk2 against cdc25c, it is similarly drawn to blocking the activity of Chk2 against one or more of its other protein targets. Additional Chk2 protein targets are E2F-1, p53, cdc25a, BRCA-1, PML, Che-1, Hdmx, Trf2, FoxM1, pRB or mdm2, for example. Further, the invention is drawn to blocking the downregulatory activity of Chk1 against not only cdc25c, but also p53, cdc25a, cdc25b, Rad51, poly-A-binding protein, aurora-B, tousled-like kinase-1, wee-1 or BLM, for example.

The following examples are included to demonstrate certain embodiments of the invention.

EXAMPLES

A study was conducted to identify short peptides applicable for preventing or reducing toxicity in the skin that can result from exposure to a mutagen or irritant. Given the prior known inhibitory effects of caffeine on the DNA damage repair pathway and the anti-cancer effects of this inhibition in epidermis, certain related peptides were assayed for the ability to similarly inhibit the DNA damage repair pathway. To this end, peptides were tested for the ability to block the Chk2 (checkpoint kinase 2)—cdc25c (cell division cycle 25 homolog C protein) arm of the DNA damage repair pathway.

Chk2, which is activated by DNA damage-sensing proteins, induces cell cycle arrest by phosphorylating and thereby inhibiting cdc25c, which is a phosphatase involved in upregulating cyclin-dependent kinase activity leading to mitosis. The interaction of these proteins in the DNA damage repair pathway and their interaction with the agents discussed below is summarized in the following schematic:

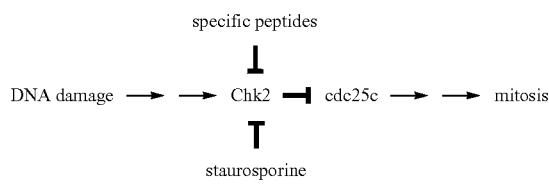

Peptides were developed to inhibit Chk2 deactivation of cdc25c using the following methodology. All peptides were synthesized using standard Fmoc chemistry on an Advanced ChemTech (Louisville, KY) APEX 396 Multiple Peptide Synthesizer. After cleavage, the peptides were purified via HPLC using a reverse phase C-18 column and then analyzed by mass spectrometry. Primary sequence confirmation and preparative purification were accomplished using an LC/MS/MS system (ABI API2000). All of the peptides used in this particular example (SEQ ID NOs:2-6 and 8-10) were carboxy-terminal amidated (-CONH$_2$).

The inhibitory activity of SEQ ID NOs:2-6 and 8-10 on Chk2 phosphorylation of cdc25c was measured using the K-LISA™ Checkpoint Activity Kit available from Calbiochem/EMD Biosciences (San Diego, CA) per the manufacturer's instructions. Activated human Chk2enzyme for these tests was obtained from Sigma (St. Louis, MO). The general kinase inhibitor, staurosporine (10 μM final concentration) was used as a positive control for the inhibition of Chk2 activity. Individual test peptides (SEQ ID NOs:2-6, 8-10) were incubated with Chk2 at a final concentration of 50 μg/mL. Briefly, the assay utilized a biotinylated peptide substrate (KKKVSRSGLYRSPSMPENLNRPR, SEQ ID NO:12) that can be phosphorylated on the third serine by Chk2 (can also be phosphorylated by Chk1 protein). This substrate served as a surrogate for cdc25c, since SEQ ID NO:12 contains the sequence targeted for serine phosphorylation by Chk2.

The biotinylated substrate peptide and sample containing Chk2 with or without added agents (staurosporine or one of SEQ ID NOs:2-6, 8-10) were incubated in the presence of ATP in wells of a streptavidin-coated 96-well plate. This incubation allowed for substrate phosphorylation by Chk2 and substrate capture in a single step. Following incubation, the phosphorylated substrate was detected using an anti-phosphoserine primary antibody, a horseradish peroxidase (HRP)-conjugated secondary antibody and TMB (tetramethylbenzidine) substrate for color development (the primary and secondary antibodies, and TMB, were provided in the K-LISA™ Checkpoint Activity Kit). Assay sensitivity was increased by the addition of the Stop solution provided in the kit. Relative Chk2 activity was determined by reading the absorbance of each well at dual wavelengths 450/540 nm.

SEQ ID NOs:2, 3, 5, 6, 8 and 10 all inhibited the activity of Chk2 against the substrate peptide (FIG. 2). For example, SEQ ID NO:10 reduced Chk2 phosphorylation activity by about 48%, which approached the inhibitory activity exhibited by staurosporine (about 69%). SEQ ID NOs:5, 6 and 8 had a similar capacity to inhibit Chk2. Overall, these data indicate that certain peptides can reduce Chk2 activity towards its substrate (i.e., cdc25c), further indicating a capacity to reduce the level of cell cycle arrest that would be initiated in vivo upon cellular exposure to DNA-damaging agents.

All of the compositions or methods disclosed and claimed herein can be made and executed without undue experimentation in light of the present disclosure. While the compositions and methods of this invention have been described in terms of certain embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention.

All patents and publications identified in this application are hereby incorporated by reference in their entirety.

The invention claimed is:

1. A method of reducing the activity of an activated cell cycle checkpoint kinase, wherein said method comprises exposing said checkpoint kinase to a peptide, wherein said peptide sequence is SEQ ID NO: 2, 3, 5, 6, 8 or 10.

2. The method of claim 1, wherein said peptide is SEQ ID NO:10.

3. The method of claim 1, wherein said peptide is SEQ ID NO:2, 3, 5, 6, or 8.

4. The method of claim 1, wherein said peptide is amidated at its carboxy terminus.

5. The method of claim 1, wherein said checkpoint kinase is checkpoint kinase-2 (Chk2).

6. A peptide for reducing the activity of an activated cell cycle checkpoint kinase, said peptide consisting of the peptide sequence of SEQ ID NOs: 3, 5, 6, 8 or 10.

7. The peptide of claim 6, wherein said peptide is SEQ ID NO:10.

8. The peptide of claim 6, wherein said peptide is SEQ ID NO: 3, 5, 6, or 8.

9. The peptide of claim 6, wherein said peptide is amidated at its carboxy terminus.

10. A composition comprising a peptide according to claim 6 and a pharmaceutically acceptable carrier.

* * * * *

SEQUENCE LISTING

```
<160> NUMBER OF SEQ ID NOS: 19

<210> SEQ ID NO 1
<211> LENGTH: 10
<212> TYPE: PRT
<213> ORGANISM: Homo Sapiens

<400> SEQUENCE: 1

Asp Tyr His Thr Leu Tyr Gln Thr His Leu
1               5                   10

<210> SEQ ID NO 2
<211> LENGTH: 9
<212> TYPE: PRT
```

```
<213> ORGANISM: Homo sapiens

<400> SEQUENCE: 2

Tyr His Ser Leu Tyr Gln Ser His Leu
1               5

<210> SEQ ID NO 3
<211> LENGTH: 9
<212> TYPE: PRT
<213> ORGANISM: Homo Sapiens

<400> SEQUENCE: 3

Tyr His Ser Ile Tyr Gln Ser His Ile
1               5

<210> SEQ ID NO 4
<211> LENGTH: 9
<212> TYPE: PRT
<213> ORGANISM: Homo sapiens

<400> SEQUENCE: 4

Asp Phe His Ser Leu Phe Gln Ser His
1               5

<210> SEQ ID NO 5
<211> LENGTH: 8
<212> TYPE: PRT
<213> ORGANISM: Homo sapiens

<400> SEQUENCE: 5

Tyr His Ser Leu Tyr Glu Ser Lys
1               5

<210> SEQ ID NO 6
<211> LENGTH: 8
<212> TYPE: PRT
<213> ORGANISM: Homo sapiens

<400> SEQUENCE: 6

Phe His Ser Ile Tyr Gln Ser His
1               5

<210> SEQ ID NO 7
<211> LENGTH: 7
<212> TYPE: PRT
<213> ORGANISM: Homo sapiens

<400> SEQUENCE: 7

Phe Lys Ser Leu Tyr Gln Ser
1               5

<210> SEQ ID NO 8
<211> LENGTH: 7
<212> TYPE: PRT
<213> ORGANISM: Homo sapiens

<400> SEQUENCE: 8

His Ser Leu Tyr Gln Ser His
1               5

<210> SEQ ID NO 9
<211> LENGTH: 6
<212> TYPE: PRT
<213> ORGANISM: Homo sapiens

<400> SEQUENCE: 9
```

-continued

```
His Ser Leu Tyr Gln Ser
1               5

<210> SEQ ID NO 10
<211> LENGTH: 5
<212> TYPE: PRT
<213> ORGANISM: Homo sapiens

<400> SEQUENCE: 10

Ser Leu Tyr Gln Ser
1               5

<210> SEQ ID NO 11
<211> LENGTH: 529
<212> TYPE: PRT
<213> ORGANISM: Homo sapiens

<400> SEQUENCE: 11

Met Leu Leu Ala Val Leu Tyr Cys Leu Leu Trp Ser Phe Gln Thr Ser
1               5                   10                  15

Ala Gly His Phe Pro Arg Ala Cys Val Ser Ser Lys Asn Leu Met Glu
            20                  25                  30

Lys Glu Cys Cys Pro Pro Trp Ser Gly Asp Arg Ser Pro Cys Gly Gln
        35                  40                  45

Leu Ser Gly Arg Gly Ser Cys Gln Asn Ile Leu Leu Ser Asn Ala Pro
    50                  55                  60

Leu Gly Pro Gln Phe Pro Phe Thr Gly Val Asp Asp Arg Glu Ser Trp
65                  70                  75                  80

Pro Ser Val Phe Tyr Asn Arg Thr Cys Gln Cys Ser Gly Asn Phe Met
                85                  90                  95

Gly Phe Asn Cys Gly Asn Cys Lys Phe Gly Phe Trp Gly Pro Asn Cys
            100                 105                 110

Thr Glu Arg Arg Leu Leu Val Arg Arg Asn Ile Phe Asp Leu Ser Ala
        115                 120                 125

Pro Glu Lys Asp Lys Phe Phe Ala Tyr Leu Thr Leu Ala Lys His Thr
    130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Tyr
            180                 185                 190

Glu Ile Trp Arg Asp Ile Asp Phe Ala His Glu Ala Pro Ala Phe Leu
        195                 200                 205

Pro Trp His Arg Leu Phe Leu Leu Arg Trp Glu Gln Glu Ile Gln Lys
    210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
                245                 250                 255

Pro Thr Asn Pro Asn Leu Leu Ser Pro Ala Ser Phe Phe Ser Ser Trp
            260                 265                 270

Gln Ile Val Cys Ser Arg Leu Glu Glu Tyr Asn Ser His Gln Ser Leu
        275                 280                 285

Cys Asn Gly Thr Pro Glu Gly Pro Leu Arg Arg Asn Pro Gly Asn His
    290                 295                 300
```

```
Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
            325                 330                 335

Asn Phe Ser Phe Arg Asn Thr Leu Glu Gly Phe Ala Ser Pro Leu Thr
        340                 345                 350

Gly Ile Ala Asp Ala Ser Gln Ser Ser Met His Asn Ala Leu His Ile
    355                 360                 365

Tyr Met Asn Gly Thr Met Ser Gln Val Gln Gly Ser Ala Asn Asp Pro
370                 375                 380

Ile Phe Leu Leu His His Ala Phe Val Asp Ser Ile Phe Glu Gln Trp
385                 390                 395                 400

Leu Arg Arg His Arg Pro Leu Gln Glu Val Tyr Pro Glu Ala Asn Ala
                405                 410                 415

Pro Ile Gly His Asn Arg Glu Ser Tyr Met Val Pro Phe Ile Pro Leu
            420                 425                 430

Tyr Arg Asn Gly Asp Phe Phe Ile Ser Ser Lys Asp Leu Gly Tyr Asp
        435                 440                 445

Tyr Ser Tyr Leu Gln Asp Ser Asp Pro Asp Ser Phe Gln Asp Tyr Ile
    450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
                485                 490                 495

Ser Leu Leu Cys Arg His Lys Arg Lys Gln Leu Pro Glu Glu Lys Gln
            500                 505                 510

Pro Leu Leu Met Glu Lys Glu Asp Tyr His Ser Leu Tyr Gln Ser His
        515                 520                 525

Leu

<210> SEQ ID NO 12
<211> LENGTH: 23
<212> TYPE: PRT
<213> ORGANISM: Artificial sequence
<220> FEATURE:
<223> OTHER INFORMATION: kinase substrate

<400> SEQUENCE: 12

Lys Lys Lys Val Ser Arg Ser Gly Leu Tyr Arg Ser Pro Ser Met Pro
1               5                   10                  15

Glu Asn Leu Asn Arg Pro Arg
            20

<210> SEQ ID NO 13
<211> LENGTH: 5
<212> TYPE: PRT
<213> ORGANISM: Homo Sapiens
<220> FEATURE:
<221> NAME/KEY: SITE
<222> LOCATION: (2)..(2)
<223> OTHER INFORMATION: Leu or Ile
<220> FEATURE:
<221> NAME/KEY: SITE
<222> LOCATION: (4)..(4)
<223> OTHER INFORMATION: Gln or Glu

<400> SEQUENCE: 13

Ser Xaa Tyr Xaa Ser
1               5
```

-continued

```
<210> SEQ ID NO 14
<211> LENGTH: 5
<212> TYPE: PRT
<213> ORGANISM: Homo sapiens

<400> SEQUENCE: 14

Ser Ile Tyr Gln Ser
1               5

<210> SEQ ID NO 15
<211> LENGTH: 5
<212> TYPE: PRT
<213> ORGANISM: Homo sapiens

<400> SEQUENCE: 15

Ser Leu Tyr Glu Ser
1               5

<210> SEQ ID NO 16
<211> LENGTH: 5
<212> TYPE: PRT
<213> ORGANISM: Homo sapiens

<400> SEQUENCE: 16

Ser Ile Tyr Glu Ser
1               5

<210> SEQ ID NO 17
<211> LENGTH: 543
<212> TYPE: PRT
<213> ORGANISM: Homo sapiens

<400> SEQUENCE: 17

Met Ser Arg Glu Ser Asp Val Glu Ala Gln Gln Ser His Gly Ser Ser
1               5                   10                  15

Ala Cys Ser Gln Pro His Gly Ser Val Thr Gln Ser Gln Gly Ser Ser
                20                  25                  30

Ser Gln Ser Gln Gly Ile Ser Ser Ser Thr Ser Thr Met Pro Asn
            35                  40                  45

Ser Ser Gln Ser Ser His Ser Ser Ser Gly Thr Leu Ser Ser Leu Glu
    50                  55                  60

Thr Val Ser Thr Gln Glu Leu Tyr Ser Ile Pro Glu Asp Gln Glu Pro
65                  70                  75                  80

Glu Asp Gln Glu Pro Glu Glu Pro Thr Pro Ala Pro Trp Ala Arg Leu
                85                  90                  95

Trp Ala Leu Gln Asp Gly Phe Ala Asn Leu Glu Cys Val Asn Asp Asn
                100                 105                 110

Tyr Trp Phe Gly Arg Asp Lys Ser Cys Glu Tyr Cys Phe Asp Glu Pro
                115                 120                 125

Leu Leu Lys Arg Thr Asp Lys Tyr Arg Thr Tyr Ser Lys Lys His Phe
            130                 135                 140

Arg Ile Phe Arg Glu Val Gly Pro Lys Asn Ser Tyr Ile Ala Tyr Ile
145                 150                 155                 160

Glu Asp His Ser Gly Asn Gly Thr Phe Val Asn Thr Glu Leu Val Gly
                165                 170                 175

Lys Gly Lys Arg Arg Pro Leu Asn Asn Asn Ser Glu Ile Ala Leu Ser
            180                 185                 190

Leu Ser Arg Asn Lys Val Phe Val Phe Phe Asp Leu Thr Val Asp Asp
            195                 200                 205

Gln Ser Val Tyr Pro Lys Ala Leu Arg Asp Glu Tyr Ile Met Ser Lys
```

```
            210                 215                 220
Thr Leu Gly Ser Gly Ala Cys Gly Glu Val Lys Leu Ala Phe Glu Arg
225                 230                 235                 240

Lys Thr Cys Lys Lys Val Ala Ile Lys Ile Ile Ser Lys Arg Lys Phe
                245                 250                 255

Ala Ile Gly Ser Ala Arg Glu Ala Asp Pro Ala Leu Asn Val Glu Thr
            260                 265                 270

Glu Ile Glu Ile Leu Lys Lys Leu Asn His Pro Cys Ile Ile Lys Ile
        275                 280                 285

Lys Asn Phe Phe Asp Ala Glu Asp Tyr Tyr Ile Val Leu Glu Leu Met
    290                 295                 300

Glu Gly Gly Glu Leu Phe Asp Lys Val Val Gly Asn Lys Arg Leu Lys
305                 310                 315                 320

Glu Ala Thr Cys Lys Leu Tyr Phe Tyr Gln Met Leu Leu Ala Val Gln
                325                 330                 335

Tyr Leu His Glu Asn Gly Ile Ile His Arg Asp Leu Lys Pro Glu Asn
            340                 345                 350

Val Leu Leu Ser Ser Gln Glu Glu Asp Cys Leu Ile Lys Ile Thr Asp
        355                 360                 365

Phe Gly His Ser Lys Ile Leu Gly Glu Thr Ser Leu Met Arg Thr Leu
    370                 375                 380

Cys Gly Thr Pro Thr Tyr Leu Ala Pro Glu Val Leu Val Ser Val Gly
385                 390                 395                 400

Thr Ala Gly Tyr Asn Arg Ala Val Asp Cys Trp Ser Leu Gly Val Ile
                405                 410                 415

Leu Phe Ile Cys Leu Ser Gly Tyr Pro Pro Phe Ser Glu His Arg Thr
            420                 425                 430

Gln Val Ser Leu Lys Asp Gln Ile Thr Ser Gly Lys Tyr Asn Phe Ile
        435                 440                 445

Pro Glu Val Trp Ala Glu Val Ser Glu Lys Ala Leu Asp Leu Val Lys
    450                 455                 460

Lys Leu Leu Val Val Asp Pro Lys Ala Arg Phe Thr Thr Glu Glu Ala
465                 470                 475                 480

Leu Arg His Pro Trp Leu Gln Asp Glu Asp Met Lys Arg Lys Phe Gln
                485                 490                 495

Asp Leu Leu Ser Glu Glu Asn Glu Ser Thr Ala Leu Pro Gln Val Leu
            500                 505                 510

Ala Gln Pro Ser Thr Ser Arg Lys Arg Pro Arg Glu Gly Glu Ala Glu
        515                 520                 525

Gly Ala Glu Thr Thr Lys Arg Pro Ala Val Cys Ala Ala Val Leu
    530                 535                 540

<210> SEQ ID NO 18
<211> LENGTH: 476
<212> TYPE: PRT
<213> ORGANISM: Homo sapiens

<400> SEQUENCE: 18

Met Ala Val Pro Phe Val Glu Asp Trp Asp Leu Val Gln Thr Leu Gly
1               5                   10                  15

Glu Gly Ala Tyr Gly Glu Val Gln Leu Ala Val Asn Arg Val Thr Glu
            20                  25                  30

Glu Ala Val Ala Val Lys Ile Val Asp Met Lys Arg Ala Val Asp Cys
        35                  40                  45

Pro Glu Asn Ile Lys Lys Glu Ile Cys Ile Asn Lys Met Leu Asn His
```

```
                50                  55                  60
Glu Asn Val Val Lys Phe Tyr Gly His Arg Arg Glu Gly Asn Ile Gln
 65                  70                  75                  80

Tyr Leu Phe Leu Glu Tyr Cys Ser Gly Gly Glu Leu Phe Asp Arg Ile
                 85                  90                  95

Glu Pro Asp Ile Gly Met Pro Glu Pro Asp Ala Gln Arg Phe Phe His
                100                 105                 110

Gln Leu Met Ala Gly Val Val Tyr Leu His Gly Ile Gly Ile Thr His
                115                 120                 125

Arg Asp Ile Lys Pro Glu Asn Leu Leu Leu Asp Glu Arg Asp Asn Leu
130                 135                 140

Lys Ile Ser Asp Phe Gly Leu Ala Thr Val Phe Arg Tyr Asn Asn Arg
145                 150                 155                 160

Glu Arg Leu Leu Asn Lys Met Cys Gly Thr Leu Pro Tyr Val Ala Pro
                165                 170                 175

Glu Leu Leu Lys Arg Arg Glu Phe His Ala Glu Pro Val Asp Val Trp
                180                 185                 190

Ser Cys Gly Ile Val Leu Thr Ala Met Leu Ala Gly Glu Leu Pro Trp
                195                 200                 205

Asp Gln Pro Ser Asp Ser Cys Gln Glu Tyr Ser Asp Trp Lys Glu Lys
210                 215                 220

Lys Thr Tyr Leu Asn Pro Trp Lys Lys Ile Asp Ser Ala Pro Leu Ala
225                 230                 235                 240

Leu Leu His Lys Ile Leu Val Glu Asn Pro Ser Ala Arg Ile Thr Ile
                245                 250                 255

Pro Asp Ile Lys Lys Asp Arg Trp Tyr Asn Lys Pro Leu Lys Lys Gly
                260                 265                 270

Ala Lys Arg Pro Arg Val Thr Ser Gly Gly Val Ser Glu Ser Pro Ser
                275                 280                 285

Gly Phe Ser Lys His Ile Gln Ser Asn Leu Asp Phe Ser Pro Val Asn
                290                 295                 300

Ser Ala Ser Ser Glu Glu Asn Val Lys Tyr Ser Ser Ser Gln Pro Glu
305                 310                 315                 320

Pro Arg Thr Gly Leu Ser Leu Trp Asp Thr Ser Pro Ser Tyr Ile Asp
                325                 330                 335

Lys Leu Val Gln Gly Ile Ser Phe Ser Gln Pro Thr Cys Pro Asp His
                340                 345                 350

Met Leu Leu Asn Ser Gln Leu Leu Gly Thr Pro Gly Ser Ser Gln Asn
                355                 360                 365

Pro Trp Gln Arg Leu Val Lys Arg Met Thr Arg Phe Phe Thr Lys Leu
                370                 375                 380

Asp Ala Asp Lys Ser Tyr Gln Cys Leu Lys Glu Thr Cys Glu Lys Leu
385                 390                 395                 400

Gly Tyr Gln Trp Lys Lys Ser Cys Met Asn Gln Val Thr Ile Ser Thr
                405                 410                 415

Thr Asp Arg Arg Asn Asn Lys Leu Ile Phe Lys Val Asn Leu Leu Glu
                420                 425                 430

Met Asp Asp Lys Ile Leu Val Asp Phe Arg Leu Ser Lys Gly Asp Gly
                435                 440                 445

Leu Glu Phe Lys Arg His Phe Leu Lys Ile Lys Gly Lys Leu Ile Asp
                450                 455                 460

Ile Val Ser Ser Gln Lys Val Trp Leu Pro Ala Thr
465                 470                 475
```

```
<210> SEQ ID NO 19
<211> LENGTH: 473
<212> TYPE: PRT
<213> ORGANISM: Homo sapiens

<400> SEQUENCE: 19

Met Ser Thr Glu Leu Phe Ser Ser Thr Arg Glu Gly Ser Ser Gly
1               5                   10                  15

Ser Gly Pro Ser Phe Arg Ser Asn Gln Arg Lys Met Leu Asn Leu Leu
            20                  25                  30

Leu Glu Arg Asp Thr Ser Phe Thr Val Cys Pro Asp Val Pro Arg Thr
                35                  40                  45

Pro Val Gly Lys Phe Leu Gly Asp Ser Ala Asn Leu Ser Ile Leu Ser
    50                  55                  60

Gly Gly Thr Pro Lys Arg Cys Leu Asp Leu Ser Asn Leu Ser Ser Gly
65                  70                  75                  80

Glu Ile Thr Ala Thr Gln Leu Thr Thr Ser Ala Asp Leu Asp Glu Thr
                85                  90                  95

Gly His Leu Asp Ser Ser Gly Leu Gln Glu Val His Leu Ala Gly Met
            100                 105                 110

Asn His Asp Gln His Leu Met Lys Cys Ser Pro Ala Gln Leu Leu Cys
        115                 120                 125

Ser Thr Pro Asn Gly Leu Asp Arg Gly His Arg Lys Arg Asp Ala Met
130                 135                 140

Cys Ser Ser Ser Ala Asn Lys Glu Asn Asp Asn Gly Asn Leu Val Asp
145                 150                 155                 160

Ser Glu Met Lys Tyr Leu Gly Ser Pro Ile Thr Thr Val Pro Lys Leu
                165                 170                 175

Asp Lys Asn Pro Asn Leu Gly Glu Asp Gln Ala Glu Glu Ile Ser Asp
            180                 185                 190

Glu Leu Met Glu Phe Ser Leu Lys Asp Gln Glu Ala Lys Val Ser Arg
        195                 200                 205

Ser Gly Leu Tyr Arg Ser Pro Ser Met Pro Glu Asn Leu Asn Arg Pro
210                 215                 220

Arg Leu Lys Gln Val Glu Lys Phe Lys Asp Asn Thr Ile Pro Asp Lys
225                 230                 235                 240

Val Lys Lys Lys Tyr Phe Ser Gly Gln Gly Lys Leu Arg Lys Gly Leu
                245                 250                 255

Cys Leu Lys Lys Thr Val Ser Leu Cys Asp Ile Thr Ile Thr Gln Met
            260                 265                 270

Leu Glu Glu Asp Ser Asn Gln Gly His Leu Ile Gly Asp Phe Ser Lys
        275                 280                 285

Val Cys Ala Leu Pro Thr Val Ser Gly Lys His Gln Asp Leu Lys Tyr
290                 295                 300

Val Asn Pro Glu Thr Val Ala Ala Leu Leu Ser Gly Lys Phe Gln Gly
305                 310                 315                 320

Leu Ile Glu Lys Phe Tyr Val Ile Asp Cys Arg Tyr Pro Tyr Glu Tyr
                325                 330                 335

Leu Gly Gly His Ile Gln Gly Ala Leu Asn Leu Tyr Ser Gln Glu Glu
            340                 345                 350

Leu Phe Asn Phe Phe Leu Lys Lys Pro Ile Val Pro Leu Asp Thr Gln
        355                 360                 365

Lys Arg Ile Ile Ile Val Phe His Cys Glu Phe Ser Ser Glu Arg Gly
370                 375                 380
```

```
                                            -continued

Pro Arg Met Cys Arg Cys Leu Arg Glu Glu Asp Arg Ser Leu Asn Gln
385                 390                 395                 400

Tyr Pro Ala Leu Tyr Tyr Pro Glu Leu Tyr Ile Leu Lys Gly Gly Tyr
                405                 410                 415

Arg Asp Phe Phe Pro Glu Tyr Met Glu Leu Cys Glu Pro Gln Ser Tyr
            420                 425                 430

Cys Pro Met His His Gln Asp His Lys Thr Glu Leu Leu Arg Cys Arg
        435                 440                 445

Ser Gln Ser Lys Val Gln Glu Gly Glu Arg Gln Leu Arg Glu Gln Ile
    450                 455                 460

Ala Leu Leu Val Lys Asp Met Ser Pro
465                 470
```